United States Patent [19]

Georgiev et al.

[11] Patent Number: 4,739,074

[45] Date of Patent: Apr. 19, 1988

[54] ADAMANTANE SPIRO-PYRROLIDINE DERIVATIVES

[75] Inventors: Vassil S. Georgiev, Rochester; George B. Mullen, Avon, both of N.Y.

[73] Assignee: Pennwalt Corporation, Philadelphia, Pa.

[21] Appl. No.: 821,293

[22] Filed: Jan. 22, 1986

[51] Int. Cl.$^4$ .................. C07D 209/96; C07D 261/20; A61K 31/40

[52] U.S. Cl. ..................................... 548/411; 548/241

[58] Field of Search ......................................... 548/411

[56] References Cited

U.S. PATENT DOCUMENTS 4,692,515 9/1987 Georgiev ............................ 540/203

OTHER PUBLICATIONS

Hennion, Chem. Abs. 66, 104861(k) 1967.

*Primary Examiner*—Mark L. Berch

[57] ABSTRACT

Adamantane spiro-pyrrolidine derivatives, more specifically, spiro[pyrrolidine-5,2'-tricyclo[3.3.1.1$^{3,7}$]decane]-derivatives of the structure

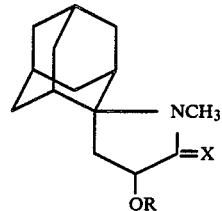

where X is oxygen or two hydrogen radicals and R is hydrogen or

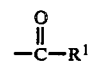

where $R^1$ is a $C_1$–$C_{18}$ alkyl radical, phenyl or phenylcyclopropyl, are disclosed herein. Said derivatives have been found to have activity in laboratory animal models against carrageenan-induced edema.

10 Claims, No Drawings

ADAMANTANE SPIRO-PYRROLIDINE DERIVATIVES

FIELD OF THE INVENTION

This invention relates to new adamantane spiro-pyrrolidine derivatives. More particularly, it relates to derivatives of spiro[pyrrolidine-5,2'-tricyclo[3.3.1.1$^{3,7}$]decane]. These compounds, when tested, were found to have anti-inflammatory activity against carrageenan-induced edema in a laboratory animal model. Additionally, some of these compounds were shown to have antiviral, antiParkinsons and antihypoxic activity when tested in laboratory animals.

STATEMENT OF THE INVENTION

This invention includes derivatives of a spiro[pyrrolidine-5,2'-tricyclo[3.3.1.1$^{3,7}$]decane] having the structural formula

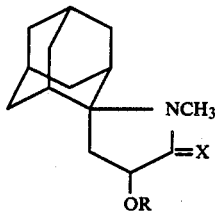

where X is oxygen or two hydrogen radicals and R is hydrogen or

where R$^1$ is a C$_1$–C$_{18}$ alkyl, a phenyl or a phenylcyclopropyl radical.

DETAILED DESCRIPTION OF THE INVENTION

The compounds of this invention are derivatives of spiro[pyrrolidine-5,2'-tricyclo[3.3.1.1$^{3,7}$]decane] of the structural formula set forth above.

The X substituent of the formula may represent two independently bonded hydrogen radicals but is preferably oxygen. R is hydrogen or

where R$^1$ is an alkyl radical having from 1 to 18 carbon atoms, preferably less than four carbons or from 14 to 16 carbons, or phenyl or phenylcyclopropyl.

In general, the adamantane spiro-pyrrolidinone derivatives of this invention are prepared by condensing 2-adamantanone in an inert atmosphere with N-methylhydroxylamine, usually dissolved in an inert organic solvent, to provide the corresponding adamantyl nitrone. The latter compound is then reacted with a substituted olefin, for example allyl alcohol or methyl acrylate, and undergoes 1,3-dipolar cycloaddition to provide an adamantanyl isoxazolidine derivative 1 821,292 filed of even date herewith. As shown in the following scheme, catalytic hydrogenolysis of the nitrogen-oxygen bond of the oxazolidine ring of the spiro[isoxazolidine-3,2'-tricyclo[3.3.1.1$^{3,7}$]decane] 1 furnishes the corresponding amino alcohol 2 which is not isolated but undergoes an immediate cyclization to supply two pyrrolidine derivatives 3 or 4. The latter compounds may be further reacted with an appropriate compound to replace the hydrogen of the hydroxyl substituent with an

group.

SCHEME

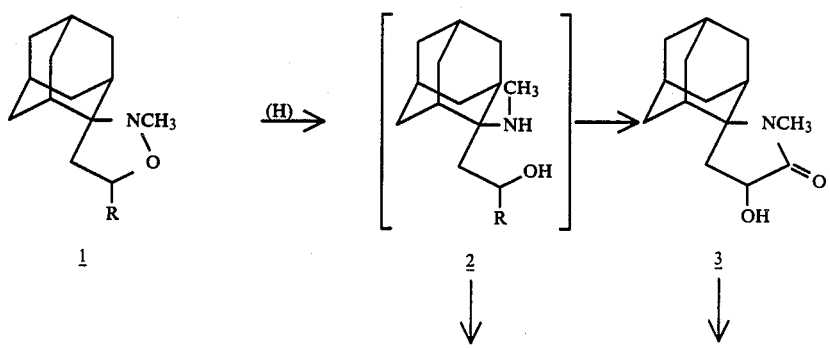

SCHEME

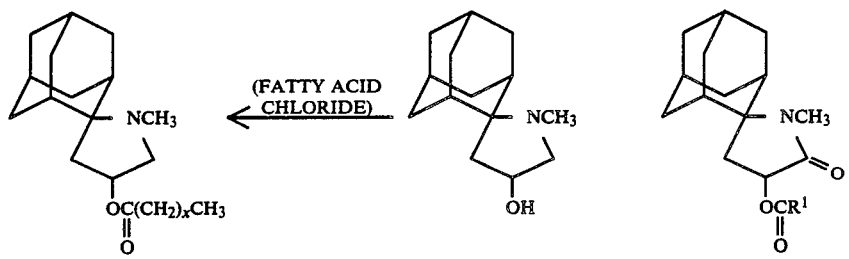

4

EXAMPLES

2-Methyl-5-hydroxymethyl-spiro[isoxazolidine-3,2'-tricyclo[3.3.1.1$^{3,7}$]decane], the compound used to prepare the starting compound for Example 9, was first prepared as follows:

Under a nitrogen atmosphere, 36.00 g (0.240 mol) of 2-adamantanone and 20.02 g (0.240 mol) of N-methylhydroxylamine hydrochloride were dissolved in 600 ml of absolute ethanol. Sodium bicarbonate (21.10 g, 0.251 mol) was added and the resulting suspension was refluxed for 3 hours. Upon cooling to room temperature, the solvent was removed in vacuo, 600 ml of toluene was added and the suspension was filtered. Allyl alcohol (25 ml, 1.5 equivalent) was added to the filtrate and the solution was refluxed under nitrogen for 18 hours. Upon cooling to room temperature, the solution was washed with water, then dried over MgSO$_4$. Removal of the solvent in vacuo gave a yellow oil which crystallized from an ether-pentane mixture (1/1) to provide 30.08 g (53%) of the above mentioned isoxazolidine compound. Recrystallization from pentane gave an analytical sample, mp 93°–6° C.

2-Methyl-5-methoxycarbonyl-spiro[isoxazolidine-3,2'-tricyclo[3.3.1.1$^{3,7}$]decane], a starting compound for the compound of Example 1, was prepared by the above procedure by replacing allyl alcohol with methyl acrylate. Recrystallization from methanol gave an analytical sample, mp 166°–170° C.

The following examples demonstrate the preparation of representative compounds of this invention.

EXAMPLE 1

1-Methyl-3-hydroxy-spiro[pyrrolidin-2-one-5,2'-tricyclo[3.3.1.1$^{3,7}$]decane], a compound of this invention, was prepared as follows:

8.16 g (0.031 mol) of 2-methyl-5-methoxycarbonyl-spiro[isoxazolidine-3,2'-tricyclo[3.3.1.1$^{3,7}$]decane], as prepared above, was hydrogenolyzed in 200 ml of glacial acetic acid in a Parr apparatus at 2 atm. over 0.8 g of a catalyst consisting of 10 wt.% palladium on 90 wt.% of an activated carbon support. After 18 hours, the suspension was suction-filtered through celite. Vacuum evaporation of the solvent gave a yellow oil which was taken up in water, made alkaline (pH 10) using 2N NaOH, and then extracted with chloroform. The organic layer was dried over MgSO$_4$ and evaporated under reduced pressure to give 6.47 g (89%) of the above identified pyrrolidinone as a white solid. An analytical sample was prepared by crystallization of the product from ethanol, mp 145°–7° C.

Anal. Calcd. for C$_{14}$H$_{21}$NO$_2$: C, 71.46; H, 8.99; N, 5.95. Found: C, 71.73; H, 9.05; N, 5.95.

This compound was found to have anti-inflammatory activity at 50 mg/kg dosage.

EXAMPLE 2

1-Methyl-3-n-hexadecanoyloxy-spiro[pyrrolidin-2-ones-5,2'-tricyclo[3.3.1.1$^{3,7}$]decane], a compound of this invention, was prepared as follows:

To 2.82 g (0.012 mol) of the pyrrolidinone prepared as described in Example 1 dissolved in 50 ml of dry THF, under a nitrogen atmosphere at 0° C., were added 2.1 ml (1.5 equivalent) of triethylamine and 3.63 g (1.1 equivalent) of palmitoyl chloride. The reaction mixture was stirred for 20 hours at room temperature, poured into ice-water and extracted with ether. The organic layer was dried over MgSO$_4$, the solvent removed in vacuo and the residual oil flash chromatographed on silica gel (Kieselgel 60, 230–400 mesh) using a 19:1 methylene chloride:methanol mixture as the eluant to give 3.64 g (64%) of the pyrrolidinone identified above. Crystallization from pentane gave an analytical sample, mp 35.5°–37.5° C.

Anal. Calcd. for C$_{30}$H$_{51}$NO$_3$: C, 76.06; H, 10.85; N, 2.96. Found: C, 76.15; H, 10.94; N, 2.80.

The compound of this example showed antiviral activity (vs. Murine cytomegalovirus). It also demonstrated antiParkinsons activity (400 mg/kg).

The procedure of Example 2 was used to prepare compounds of this invention as reported in Examples 3–8 except that palmitoyl chloride was replaced in each case with the same molar equivalency of the replacement compound identified in the example.

EXAMPLE 3

To prepare 1-methyl-3-methylcarbonyloxy-spiro[pyrrolidin-2-one-5,2'-tricyclo[3.3.1.1$^{3,7}$]decane] the replacement compound used in the procedure of Example 2 was acetyl chloride.

Crystallization from a methanol-ether mixture (1:19) gave an analytical sample, mp. 146°–149° C.

Anal. Calcd. for C$_{16}$H$_{23}$NO$_3$: C, 69.29; H, 8.36; N, 5.05. Found: C, 69.33; H, 8.49; N, 5.04.

This compound showed anti-inflammatory activity at a dose of 50 mg/kg.

EXAMPLE 4

To prepare 1-methyl-3-ethylcarbonyloxy-spiro[pyrrolidin-2-one-5,2'-tricyclo[3.3.1.1$^{3,7}$]decane], the replacement compound used in the procedure of Example 2 was propionyl chloride.

Crystallization from n-propanol gave an analytical sample, mp. 157°–159° C.

Anal. Calcd. for $C_{17}H_{25}NO_3$: C, 70.07; H, 8.65; N, 4.81. Found: C, 70.04; H, 8.77; N, 4.70.

This compound showed anti-inflammatory activity at a dose of 50 mg/kg.

EXAMPLE 5

To prepare 1-methyl-3-phenylcarbonyloxy-spiro[pyrrolidin-2-one-5,2'-tricyclo[3.3.1.1$^{3,7}$]decane], the replacement compound used in the procedure of Example 2 was benzoyl chloride.

Crystallization of the product from n-propanol gave an analytical sample, mp. 113°–115° C.

Anal. Calcd. for $C_{21}H_{25}NO_3$: C, 74.31; H, 7.42; N, 4.13. Found: C, 74.32; H, 7.72; N, 4.05.

This compound demonstrated anti-inflammatory activity at a dose of 50 mg/kg.

EXAMPLE 6

To prepare 1-methyl-3-phenoxymethylcarbonyloxy-spiro[pyrrolidin-2-one-5,2'-tricyclo[3.3.1.1$^{3,7}$]decane, the replacement compound used in the procedure of Example 2 was phenoxyacetyl chloride.

Crystallization of the product from n-propanol gave an analytical sample, mp. 129°–132° C.

Anal. Calcd. for $C_{22}H_{27}NO_4$: C, 71.52; H, 7.37; N, 3.79. Found: C, 71.56; H, 7.49; N, 3.74.

EXAMPLE 7

1-Methyl-3-[(2-phenylcyclopropyl)carbonyloxy-spiro[pyrrolidin-2-one-5,2'-tricyclo[3.3.1.1$^{3,7}$]decane], was prepared using the replacement compound trans-2-phenylcyclopropane-1-carboxylic acid chloride in the procedure of Example 2.

Crystallization of the product with benzene gave an analytical sample (isomer A), mp. 184°–186° C.

Crystallization of the product with ethyl acetate gave an analytical sample (isomer B), mp. 169°–172° C.

Anal. (of A & B) Calcd. for $C_{24}H_{29}NO_3$: C, 75.96; H, 7.70; N, 3.69. Found (A): C, 75.97; H, 7.74; N, 3.88. Found (B): C, 76.17; H, 7.82; N, 3.72.

Isomer A showed antihypoxic activity at a dose of 100 mg/kg.

EXAMPLE 8

To prepare 1-methyl-3-cinnamoyloxy-spiro[pyrrolidin-2-one-5,2'-tricyclo[3.3.1.1$^{3,7}$]decane], the replacement compound used in the procedure of Example 2 was cinnamoyl chloride.

Crystallization from ethyl acetate gave an analytical sample, mp. 117°–119° C.

Anal. Calcd. for $C_{23}H_{27}NO_3$: C, 75.59; H, 7.45; N, 3.83. Found: C, 75.53; H, 7.58; N, 3.83.

2-Methyl-5-(methanesulfonyloxy)methyl-spiro[isoxazolidine-3,2'-tricyclo[3.3.1.1$^{3,7}$]decane]. The starting compound used to prepare the compound of Example 9, was prepared as follows:

Under a nitrogen atmosphere, 6.02 g (25.4 mmol) of the first prepared isoxazolidine compound described under a foregoing paragraph headed "Examples" were dissolved in 75 ml of dry pyridine. The solution was cooled in an ice bath, then 10.0 ml (5.0 equivalents) of methanesulfonyl chloride were added dropwise over 15 min. The resulting yellow solution was stirred for 1 hour at 5° C., and then for 2 hours at room temperature. The reaction mixture was poured into water, then cautiously neutralized with $K_2CO_3$ and extracted with methylene chloride. The organic layer was dried ($MgSO_4$), and the solvent removed in vacuo. Crystallization from a 2:1 ether-petroleum ether mixture (40°–60° C.) gave the above identified methanesulfonyloxy derivative as white flakes, 6.79 g (85%), mp 88°–90° C.

EXAMPLE 9

1-Methyl-3-hydroxy-spiro[pyrrolidine-5,2'-tricyclo[3.3.1.1$^{3,7}$]decane, a compound of this invention, was prepared as follows:

10.6 g (0.0317 mol) of the above identified methanesulfonyloxy derivative were dissolved in 90 ml of glacial acetic acid and hydrogenated in a Parr apparatus at 40 psi. over 1.0 g of a catalyst comprising 5 wt.% palladium deposited on 95 wt.% carbon. After 6 hours, the suspension was filtered and the solvent removed in vacuo. The residual oil was dissolved in water, made basic with $K_2CO_3$, and extracted with methylene chloride. The organic layer was dried ($MgSO_4$) and the solvent removed in vacuo. Crystallization from ligroin (90°–110° C.) gave 5.98 g (85%) of the above identified pyrrolidine derivative, mp. 90°–92° C.

Anal. Calcd. for $C_{14}H_{23}NO$: C, 75.97; H, 10.47; N, 6.33. Found: C, 76.02; H, 10.50; N, 6.30.

EXAMPLE 10

1-Methyl-3-n-hexadecanoyloxy-spiro[pyrrolidine-5,2'-tricyclo[3.3.1.1$^{3,7}$]decane] was prepared by hydrogenating the methanesulfonyloxy derivative of Example 9 in accordance with the procedure of Example 1 and then reacting the product with palmitoyl chloride in accordance with Example 2.

Crystallization from pentane gave an analytical sample melting at 50°–53° C.

Anal. Calcd. for $C_{30}H_{53}NO_2$: C, 78.37; H, 11.62; N, 3.05. Found: C, 78.50; H, 11.56; N, 2.78.

This compound showed anti-inflammatory activity at a dose of 50 mg/kg.

We claim:

1. An adamantane spiro-pyrrolidinone derivative having the structure

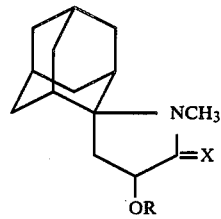

where X is oxygen or two hydrogen radicals and R is hydrogen or

where $R^1$ is an alkyl radical having from 1 to 18 carbon atoms, phenyl or phenylcyclopropyl.

2. The derivative of claim 1 wherein X is oxygen and R is

3. The derivative of claim 2 wherein $R^1$ is an alkyl radical having from 1 to 3 carbon atoms.

4. The derivative of claim 2 wherein $R^2$ is an alkyl radical having 14 to 16 carbon atoms.

5. The derivative of claim 2 wherein $R^1$ is phenyl.

6. The derivative of claim 2 wherein $R^1$ is phenylcyclopropyl.

7. The derivative of claim 1 wherein X represents two hydrogen radicals.

8. The derivative of claim 7 wherein R is hydrogen.

9. The derivative of claim 7 wherein R is $$-\overset{\overset{\displaystyle O}{\|}}{C}-R^1.$$

10. The derivative of claim 9 wherein $R^1$ is an alkyl radical having from 14 to 16 carbon atoms.